United States Patent [19]

Poisson et al.

[11] 4,272,457
[45] Jun. 9, 1981

[54] ALKALINE HEMIESTERS AND ALIPHATIC DIESTERS OF BIS-(HYDROXY-4-PHENYL) ALKYLPHOSPHONIC ACIDS

[75] Inventors: Pierre Poisson, Bernay; Georges Sturtz, Brest, both of France

[73] Assignee: Societe Anonyme dite: Ato Chimie, France

[21] Appl. No.: 104,788

[22] Filed: Dec. 18, 1979

[30] Foreign Application Priority Data

Dec. 20, 1978 [FR] France .................. 78 35753

[51] Int. Cl.³ .................................... C07F 9/40
[52] U.S. Cl. .................... 260/953; 252/400 A
[58] Field of Search ............................ 260/953

[56] References Cited

U.S. PATENT DOCUMENTS 3,676,531  7/1972  Spivack et al. ............. 260/953
3,702,879  11/1972  Bredereck et al. ........... 260/953

*Primary Examiner*—Anton H. Sutto
*Attorney, Agent, or Firm*—Bacon & Thomas

[57] ABSTRACT

Novel alkaline hemiesters of bis-(hydroxy-4-phenyl)-alkylphosphonic acids of the general formula:

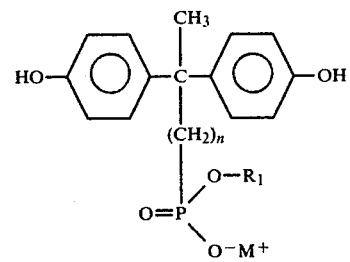

in which:
n is equal to 0, 1, 2 or 3,
M is an alkaline metal such as lithium, sodium or potassium
$R_1$ is a cyclohexyl radical or an $C_1$ to $C_6$ alkyl radical.

8 Claims, No Drawings

ALKALINE HEMIESTERS AND ALIPHATIC DIESTERS OF BIS-(HYDROXY-4-PHENYL) ALKYLPHOSPHONIC ACIDS

BACKGROUND OF THE INVENTION

The present invention concerns novel alkaline hemiesters of bis(hydroxy-4-phenyl)-alkylphosphonic acids of the general formula (I):

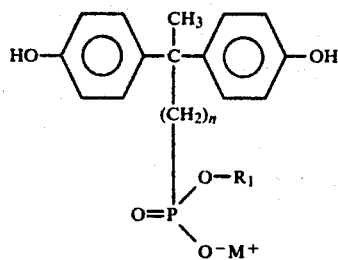

in which:
R is a cyclohexyl or aliphatic hydrocarbon radical having 1 to 6 carbon atoms,
n is equal to 0, 1, 2 or 3, and
M is an alkaline metal e.g. lithium, sodium or potassium.

These novel products may be obtained from novel dialkyl phosphonates of bis-(hydroxy-4-phenyl)-alkyl having the general formula (II):

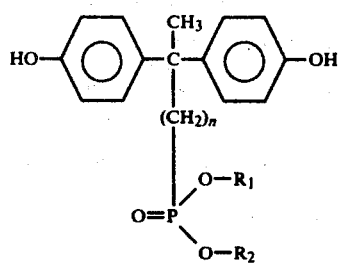

in which:
n is an integer equal to 1, 2 or 3,
$R_1$ and $R_2$ are an $C_1$ to $C_6$ aliphatic hydrocarbon radical, or of dialkyl phosphonates of bis-(hydroxy-4-phenyl)-1,1-ethyl, already known in the art, having the general formula (III):

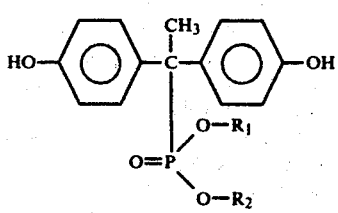

which are described along with their preparation in U.S. Pat. No. 3,702,879.

The alkaline hemiesters according to the present invention may be used as stabilisers antioxidants, or fire resisting agents for organic materials and specially plastic materials. Their difunctional phenolic character allows them to be used as polycondensation monomer or comonomer leading to such polymers as polyethers, polycarbonates, epoxy resins obtained from diphenols.

The presence of phosphonic ion can give to such plastic materials internal characteristics of stabilization, fire resistance, ion exchange or complexing agents for the metals.

Phosphonic diesters having a structure similar to that of formula (II) were described by Spivack in Belgium Pat. No. 750,593. However the diesters prepared by Spivack comprise several aliphatic or alicyclic substituents on the phenyl nucleii thus creating a hindered structure which renders these products unsuitable for polycondensation.

The alkaline hemiesters derived from formulae (II) and (III) comprise no substituent on the phenyl nuclei and therefore they can be used as polycondensation monomer with the aim of obtaining plastic material carrying phosphonic functions of the formula:

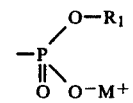

Among the hemiesters to be obtained can be cited inter alia:
sodium and methyl phosphonate of bis-(hydroxy-4-phenyl)-1,1-ethyl,
potassium and methyl phosphonate of bis-(hydroxy-4-phenyl)-1,1-ethyl,
sodium and methyl phosphonate of bis-(hydroxy-4-phenyl)-2,2-propyl,
potassium and methyl phosphonate of bis-(hydroxy-4-phenyl)-2,2-propyl,
sodium and methyl phosphonate of bis-(hydroxy-4-phenyl)-3,3-butyl.

These alkaline phosphonic hemiesters can be obtained from the diesters of the corresponding bis-(hydroxy-4-phenyl)-alkylphosphonic acids through treating the latter with either an alcohol solution of 10 to 20% by weight alkaline hydroxide, in a molar ratio alkaline hydroxide/diester of 3.2 to 3.5 or by a ketonic solution saturated with alkaline iodide, the molar ratio NaI/diester being 1.5 to 2.5.

A way of preparing alkaline hemiesters according to the present invention consists in treating at reflux during 24 hours the corresponding dialkyl phosphonates of bis-(hydroxy-4-phenyl)-alkyl by a ketonic solution of sodium iodide.

The precipitated hemiester is isolated and purified by filtration, washed with solvent and dried under vacuum.

Another way of preparing the alkaline hemiesters according to the present invention consists in treating the corresponding dialkylphosphonate of bis-(hydroxy-4-phenyl)-alkyl by an alcohol solution of NaOH at reflux during 10 to 24 hours; the precipitated sodium chloride is filtered and the solvent is evaporated to dryness under a vacuum of 0.5 to 2 mm.Hg.

U.S. Pat. No. 3,702,879 describes the preparation of phosphonates of bis-(hydroxy-4-phenyl)-1.1-ethyl from a α-ketophosphonate on which phenol has been made to react in the presence of a Lewis acid.

The novel phosphonic diesters of bis-(hydroxy-4-phenyl)-propyl, butyl or pentyl may be obtained by reaction of the β,γ or δ-ketophosphonates on phenol in the presence of a Lewis acid, preferably boron trifluoride, according to the following reaction scheme:

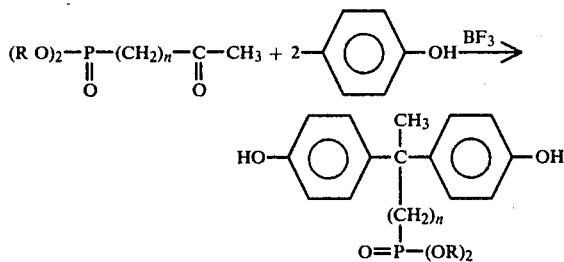

As ketophosphonic acid diesters, also called oxoalkyl phosphonate may be used, for example:
  dimethyl phosphonate of oxo-2-propyl,
  diethyl phosphonate of oxo-2-propyl,
  diethyl phosphonate of oxo-3-butyl,
  diethyl phosphonate of oxo-4-pentyl,
  dicyclohexyl phosphonate of oxo-2-propyl.

To prepare the dialkyl phosphonates of bis-(hydroxy-4-phenyl)-alkyl according to the present invention, an oxo-alkyl phosphonate is mixed with phenol in a molar ratio phenol/oxo-alkyl phosphonate of 4 to 8 and the boron trifluoride is caused to bubble in this mixture until saturation while maintaining the temperature between 10° and 30° C., and preferably between 15° and 25° C.; then the temperature is raised to about 40° to 50° C. and the condensation reaction occurs at atmospheric pressure during 30 to 60 minutes.

When the reaction is completed the product is diluted in acetic acid and the mixture is added with water which leads to the precipitation of a slowly hardening oily product. The solidified product is washed with water, centrifuged and dried. The obtained powder is purified by crystallisation in a solvent or a mixture of suitable solvents. To obtain the corresponding alkaline hemiesters the bis-(hydroxy-4-phenyl)-alkyl-phosphonate obtained is treated by an alcohol solution of NaOH or KOH at reflux during 10 to 24 hours.

Afterwards, the reaction mixture is neutralised with HCl, until pH=7 and concentrated under reduced pressure.

The precipitated sodium chloride is filtered and the evaporation of the filtrate is completed to dryness under vacuum of 1 mm.Hg.

The products are identified by elementary analysis, infrared spectrum and NMR spectrum.

The following examples are given by way of illustration without in any way limiting the present invention.

EXAMPLE 1

Dimethyl phosphonate of bis-(hydroxy-4-phenyl)-2,2-propyl 370 g of phenol (3.97 moles) are saturated in $BF_3$ between 20° and 25° C.; then, drop by drop during 30 minutes, 108 g of dimethyl phosphonate of oxo-2-propyl (0.65 mole) are introduced in the mixture while keeping the temperature lower than 20° C. Then the reaction is left to occur at room temperature. The temperature of reaction mixture rises to 30° to 35° and remains in this temperature range during one hour without heating being necessary. At the end of one hour the reaction mixture is raised to 40° C. and kept at this temperature during 30 minutes.

Then it is cooled and diluted with 320 ml acetic acid and the acetic solution is poured into 7 l of water. The resulting oil solidifies in about 20 hours. The obtained solid is washed with water, centrifuged, and dried. 184 g of a slightly coloured raw product is obtained which is re-dissolved in the dioxanne at reflux then crystallised through the addition of water, then centrifuged after cooling with ice and dried. A white powder (molar yield: 75%) which melts at 185° C. is obtained.

Elementary analysis (%): $C_{17}H_{21}PO_5$

|  | C | H | P |
|---|---|---|---|
| ~ Calculated | 60.71 | 6.25 | 9.22 |
| ~ Found | 60.77 | 6.21 | 8.34 |

Infrared spectrum:
$\delta(OH) = 3\ 300\ cm^{-1}$
$\delta(P=O) = 1\ 225\ cm^{-1}$
$\delta(P\text{-}O\text{-}C) = 1\ 050,\ 1\ 020\ cm^{-1}$ NMR spectrum ($D^+$, DMSO as solvent): (DMSO=dimethylsulfoxide)

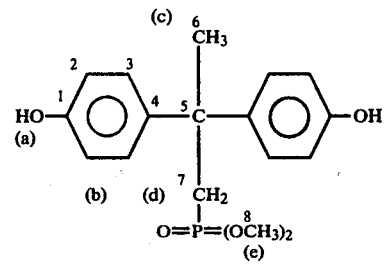

| $\delta = 9.16$ ppm (s) | 2Ha |
| $\delta = 7.15\text{-}6.55$ ppm (m) | 8Hb |
| $\delta = 3.28$ ppm (d) | 6He, JP − He = 11Hz |
| $\delta = 2.62$ ppm (d) | 2Hd, JP − Hd = 20Hz |
| $\delta = 1.76$ ppm (s) | 3Hc |

NMR $^{13}C$ spectrum (deuterated DMSO solvent):
$\delta = 156.6$ ppm $C_1$
$\delta = 140.8\text{-}141.6$ ppm $C_4$
$\delta = 129.3$ ppm $C_3$
$\delta = 116.1$ ppm $C_2$
$\delta = 52.9$ ppm $C_8$
$\delta = 43.86$ ppm $C_5$
$\delta = 34$ ppm $C_7$
$\delta = 30$ ppm $C_6$

EXAMPLE 2

Sodium and methyl phosphonate of bis-(hydroxy-4-phenyl)-2.2-propyl

In a flask equipped with a stirrer, a condensator, a thermometer and a nitrogen feed pipe, 33.6 g (0.01 mole) of dimethyl phosphonate of bis-(phenyl-4-hydroxy)-2,2-propyl is dissolved in a alcohol-water solution prepared by dissolving 0.3 mole NaOH in 27 ml water and 100 ml methanol. After having passed a nitrogen feed in the mixture, said mixture is maintained at reflux during 24 hours; then it is cooled to room temperature, and neutralised until pH 7 with concentrated HCl, under cooling. Then the mixture is concentrated under reduced pressure. The dry residue is dissolved in a small quantity of methanol and the precipitated sodium chloride is filtered; the filtrate is then concentrated under reduced pressure then dried at 150°-160° C. under vacuum of 1 mm.Hg. 32.3 g (yield: 95%) of a white, hygroscopic powder (which decomposes at about 220°-225° C.) is obtained.

The elementary analysis gives the following results as to sodium and phosphorus content (%):

|  | Na | P |
|---|---|---|
| ~ Calculated | 6.68 | 9.01 |
| ~ Found | 6.93 | 8.9 |

Determination carried out by X fluorescence regarding the phosphorus.

NMR spectrum of the proton in D$_2$O as solvent:

HO—(a)⟨(b) 2,3⟩—$^4$C$^5$(c)(CH$_3$)—⟨⟩—OH
                   |
                   $^7$CH$_2$—P(=O)(ONa)(OCH$_3$)
                   (d)        (e) 8

$\delta$ = 7.3–6.7 ppm (m)  8Hb
$\delta$ = 3.20 ppm (d)     3He, JP – He = 10.5 Hz
$\delta$ = 2.62 ppm (d)     2Hd, JP – Hd = 21.6 Hz
$\delta$ = 1.83 ppm (s)     3Hc The integration confirms the presence of a single methoxy OCH$_3$ group.

NMR spectrum of the proton deuterated in DMSO:
$\delta$ = 10–9 ppm protons Ha phenolics
$\delta$ = 3.02 ppm (d) H$_e$ NMR of $^{13}$C (D$_2$O):
$\delta$ = 155.7 ppm C$_1$
$\delta$ = 144.5–145.2 ppm C$_4$
$\delta$ = 130.9 ppm C$_3$
$\delta$ = 117.34 ppm C$_2$
$\delta$ = 53.7 ppm C$_8$
$\delta$ = 45.22 ppm C$_5$
$\delta$ = 36.4 ppm C$_7$
$\delta$ = 30.4 ppm C$_6$

EXAMPLE 3

Potassium and methyl phosphonate of bis-(hydroxy-4-phenyl)-2.2-propyl 8,4 g (0.025 mole) of dimethyl phosphonate of bis-(hydroxy-4-phenyl)-2.2-propyl is dissolved in 118 ml of a 2.6 N potassium hydroxide methanol solution. It is maintained at reflux during 28 hours. Then in order to isolate the product, a process such as described in Example 2 is followed.

The obtained product decomposes at 235° C.
Elementary analysis(%): C$_{16}$H$_{18}$PO$_5$K

|  | P | K |
|---|---|---|
| ~ Calculated | 8.61 | 10.83 |
| — Found | 8.10 | 9.42 |

NMR of the proton in D$_2$O:

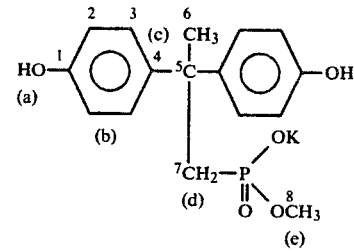

$\delta$ = 7.3–6.75 ppm (m) 8Hb
$\delta$ = 3.20 ppm (d) 3He      JP – He = 10.5 Hz
$\delta$ = 2.60 ppm (d) 2Hd      JP – Hd = 18 Hz
$\delta$ = 1.82 ppm (s) 3Hc NMR of the proton in DMSO d$_6$:

The Ha phenolic protons come out at between 10.5 and 9.5 ppm.

$\delta$ = 3.10 ppm (d) 3 He
JP-He = 10.5 Hz $^{13}$Carbon NMR in D$_2$O:
$\delta$ = 155.7 ppm C$_1$
$\delta$ = 145.3–144.6 ppm C$_4$
$\delta$ = 130.9 ppm C$_3$
$\delta$ = 117.2 ppm C$_2$
$\delta$ = 53.73–53.34 ppm C$_8$
$\delta$ = 45.22 ppm C$_5$
$\delta$ = 36.38 ppm C$_7$
$\delta$ = 30.40 ppm C$_6$

EXAMPLE IV

Preparation of diethyl phosphonate of bis-(hydroxy-4-phenyl)-2.2-propyl 97 g (0.5 mole) of diethyl phosphonate of oxo-2-propyl and 282 g (3 moles) of phenol are mixed together.

The temperature is cooled to about 10° to 15° C. and the boron trifluoride is made to bubble until saturation while maintaining the temperature of the reaction mixture lower than 25° C. The reaction mixture which has an orange color is heated to 40° C. during one hour, during which time it becomes more and more viscous and takes on a bluish red color. The reaction mass is cooled and dissolved in about 250 ml acetic acid; then the acetic solution is poured into 6 l of water. A yellow oil separates and hardens very slowly during 48 hours.

The solidified product is ground, washed several times with water under stirring, centrifuged and dried. A slightly coloured powder is obtained which is recrystallised in an ethyl ½ acetate/cyclohexane ½ mixture.

126 g of a white powder is obtained (molar yield: 69%); this powder melts at 152° C. and its IR and RMN spectrum as well as the elementary analysis confirms the following chemical structure:

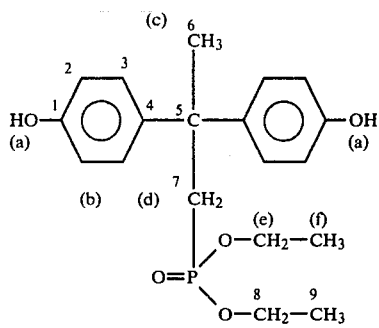

Elementary analysis (%): $C_{19}H_{25}PO_5$

|              | C     | H    | P    |
|--------------|-------|------|------|
| ~ Calculated | 62.63 | 6.86 | 8.51 |
| ~ Found      | 62.61 | 6.88 | 8.49 |

Infrared analysis:
$\nu OH = 3\ 300\ cm^{-1}$
$\nu CH$ aromatic $= 3\ 100\ cm^{-1}$
$\nu P=O = 1\ 255\ cm^{-1}$
$\nu p$—O—C $= 1\ 060\ cm^{-1}$—$1025\ cm^{-1}$—$960\ cm^{-1}$
$\delta CH$ aromatic $= 830\ cm^{-1}$ NMR $^1H$ Spectrum (deuterated in DMSO solvent):

| $\delta = 8.6$ ppm (s)      | 2Ha                    |
| $\delta = 7.2$–6,6 ppm (m)  | 8Hb                    |
| $\delta = 3.9$ ppm (q)      | 4He                    |
| $\delta = 2.72$ ppm (d)     | 2Hd, JP – Hd = 19 Hz   |
| $\delta = 1.9$ ppm (s)      | 3Hc                    |
| $\delta = 1.15$ ppm (t)     | 6Hf                    |

NMR $^{13}C$ spectrum (deuterated in DMSO solvent):
$\delta = 156.7$ ppm $C_1$
$\delta = 141.6$–140,8 ppm $C_4$
$\delta = 129.3$ ppm $C_3$
$\delta = 115.9$ ppm $C_2$
$\delta = 61.9$ ppm $C_8$
$\delta = 43.9$ ppm $C_5$
$\delta = 30.2$ ppm $C_6$
$\delta = 34.7$ ppm $C_7$
$\delta = 17.86$–17.41 ppm $C_9$

EXAMPLE 5

Sodium and ethyl phosphonate of bis-(hydroxy-4-phenyl)-2.2-propyl 36.4 g (0.1 mole) of diethyl phosphonate of bis-(hydroxy-4-phenyl)-propyle is dissolved in a NaOH alcohol solution prepared as in Example 2.

The mixture is maintained at reflux during 24 hours, cooled to room temperature and neutralized with concentrated HCl until pH=7 under cooling; at this stage, the presence of a precipitate is observed; it is identified as the initial diethyl bisphenol phosphonate. In order to eliminate totally the latter, the hot product thus obtained, after alkaline hydrolysis, is treated with a hot cyclohexane/ethyl acetate mixture.

The obtained product is in the form of a powder which decomposes at about 220°–225° C.

Elementary analysis (%): $C_{17}H_{20}PO_5Na$

|              | P    | Na   |
|--------------|------|------|
| ~ Calculated | 8.65 | 6.42 |
| ~ Found      | 8.4  | 5.78 |

NMR spectrum of the proton (in $D_2O$ solvent):

| $\delta = 7.18$–6.6 ppm (m) | 8Hb                    |
| $\delta = 3.5$ ppm (q)      | 2He                    |
| $\delta = 2.57$ ppm (d)     | 2Hd, JP – Hd = 18 Hz   |
| $\delta = 1.82$ ppm (s)     | 3Hc                    |
| $\delta = 1.05$ ppm (t)     | 3Hf                    |

EXAMPLE 6

Potassium and ethyl phosphonate of bis-(hydroxy-4-phenyl)-2.2-propyl 36.4 g (0.1 mole) of diethyl phosphonate of bis-(hydroxy-4-phenyl)-2.2-propyl are dissolved in a KOH alcohol solution prepared as in Example 3.

The mixture is maintained at reflux during 24 hours, then cooled to room temperature and neutralized with concentrated HCl until PH=7. At this stage, a sticky precipitate is observed which is eliminated by filtration.

This filtrate is concentrated to dryness, taken up by a small quantity of methanol. The precipitated sodium chloride is eliminated by filtration; the methanol filtrate is then concentrated under reduced pressure and dried under vacuum of 2 mm.Hg.

The hot product thus obtained is treated with a cyclohexane/ethyl acetate mixture, as in Example 5. The product obtained decomposes at 225°–230° C.

Elementary analysis (%): $C_{17}H_{20}PO_5K$

|              | P    | K     |
|--------------|------|-------|
| ~ Calculated | 8.28 | 10.42 |
| ~ Found      | 8    | 9.71  |

EXAMPLE 7

Preparation of dimethyl phosphonate of bis-(hydroxy-4-phenyl)-3.3-butyl

The process proceeds as in Example 1. The obtained product (yield: 86%) has the following characteristics:
Melting point: 170° C.
Elementary analysis (%): $C_{18}H_{23}PO_5$

|              | C     | H    | P    |
|--------------|-------|------|------|
| ~ Calculated | 61.71 | 6.57 | 8.85 |
| ~ Found      | 61.36 | 6.50 | 8.48 |

Infrared spectrum:
$\nu OH = 3\ 290\ cm^{-1}$
$\nu P=O = 1\ 225\ cm^{-1}$

NMR spectrum of the proton (deuterated in DMSO solvent):

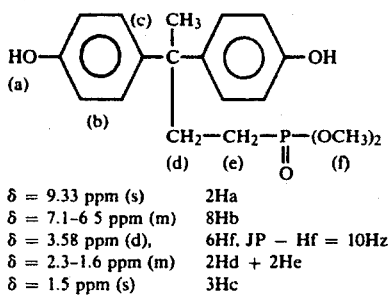

| | |
|---|---|
| δ = 9.33 ppm (s) | 2Ha |
| δ = 7.1–6.5 ppm (m) | 8Hb |
| δ = 3.58 ppm (d), | 6Hf, JP − Hf = 10Hz |
| δ = 2.3–1.6 ppm (m) | 2Hd + 2He |
| δ = 1.5 ppm (s) | 3Hc |

EXAMPLE 8

Sodium and methyl phosphonate of bis-(hydroxy-4-phenyl)-3.3-butyl 30 g of NaI are dissolved in 300 ml of acetone then 35 g (0.1 mole) of dimethyl phosphonate of bis-(hydroxy-4-phenyl)-2.2-butyl are introduced; the obtained solution is maintained at reflux during 32 hours at the end of which a large amount of precipate is formed.
This hot mixture is filtered; the precipitate is washed several times with hot acetone and then dried at 100° C. in an oven.

21 g (yield: 58%) of a white hygroscopic powder (which decomposes at 240° C.) are obtained.

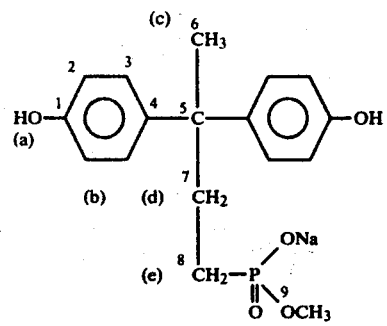

NMR of $^1$H (in D$_2$O):

| | |
|---|---|
| δ = 7.17–6.67 ppm (multiplet) | 8Hb |
| δ = 3.41 ppm (doublet) | 3Hf, JP − HF = 10Hz |
| δ = 2.36–2.02 ppm (multiplet) | He |
| δ = 1.51 ppm (singlet) | 3Hc |

The Hd protons come out between 1.5 and 1.07 (multiplet) and are partially hidden by the Hc protons.
NMR of $^{13}$C (in D$_2$O):

| | |
|---|---|
| δ = 155.80 ppm | C$_1$ |
| δ = 143.91 ppm | C$_4$ |
| δ = 131.11 ppm | C$_3$ |
| δ = 117.47 ppm | C$_2$ |
| δ = 53.92–53.60 ppm | C$_9$ |
| δ = 47.75–46.50 ppm | C$_5$ |
| δ = 37.35 ppm | C$_7$ |
| δ = 29.04 ppm | C$_6$ |
| δ = 23.42 ppm (doublet) | C$_8$ JP − C$_8$ = 133.8 |

EXAMPLE 9

Preparation of sodium and methyl phosphonate of bis-(hydroxy-4-phenyl)-1.1-ethyl by alkaline hydrolysis of dimethyl phosphonate of bis-(hydroxy-4-phenyl)-1.1-ethyl 32.2 g (0.1 mole) of dimethyl phosphonate of bis-(hydroxy-4-phenyl-1.1-ethyl which was obtained according to the process described in U.S. Pat. No. 3,702,879 are dissolved in KOH water-alcohol solution prepared according to the conditions given in Example 2.

The mixture is maintained at reflux during 24 hours, then it is proceeded to isolate the product as in Example 2.

A white powder (which decomposes at 260° C.) is obtained.

Elementary analysis (%): C$_{15}$H$_{16}$PO$_5$Na

| | P | Na |
|---|---|---|
| . Calculated | 9.39 | 6.96 |
| . Found | 8.50 | 7.17 |

NMR spectrum of the proton (in D$_2$O as solvent):

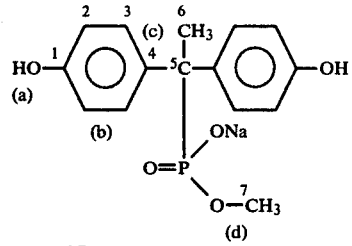

| | |
|---|---|
| δ = 7.4–6.7 ppm | 8Hb |
| δ = 3.32 ppm (d) | 3Hd, JP − Hd = 9.75 Hz |
| δ = 1.80 ppm (d) | 3Hc, JP − Hc = 15.27 Hz |

NMR of $^{13}$C (in D$_2$O):

| | |
|---|---|
| δ = 156.19 ppm | C$_1$ |
| δ = 140.53–140.27 ppm | C$_4$ |
| δ = 133.12–133.67 ppm | C$_3$ |
| δ = 117.27 ppm | C$_2$ |
| δ = 58.02 ppm | C$_7$ |
| δ = 51.00 ppm | C$_5$ JP − C$_5$ = 121 Hz |
| δ = 28.39–28.19 ppm | C$_6$ |

EXAMPLE 10

Preparation of sodium and methyl phosphonate of bis-(hydroxy-4-phenyl)-1.1-ethyl by acting of the sodium iodide on the dimethyl phosphonate of bis-phenol 24.5 g of NaI (0.163 mole) are dissolved in 250 ml of acetone, then 26 g (0.0807 mole) of dimethyl phosphonate of bis-(hydroxy-4-phenyl)-1.1-ethyl are introduced.

The mixture is maintained at reflux during 24 hours; at this stage, the presence of a sticky precipitate is observed.

The obtained product is filtered at hot, washed several times with hot acetone, then centrifuged and dried.

21 g (yield: 78,8%) of a white powder (which decomposes at about 225° C.) are obtained.

NMR spectrum of the proton (in D$_2$O):

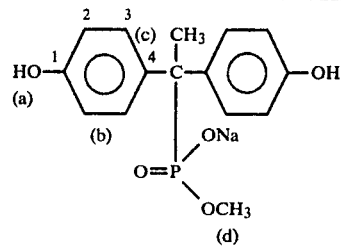

| | |
|---|---|
| δ = 7.4–6.7 ppm (m) | 8HB |
| δ = 3.30 ppm (d) | 3Hd, JP − Hd = 10.5 Hz |
| δ = 1.79 ppm (d) | 3Hc, JP − Hc = 15.0 Hz |

NMR spectrum of the proton (in DMSO d$_6$):
The Ha phenolic protons come out at 9.6 ppm.
NMR of $^{13}$C (in deuterated DMSO):

| | |
|---|---|
| δ = 156.38 ppm | C$_1$ |
| δ = 139.3–139.04 ppm | C$_4$ |
| δ = 131.5–131.1 ppm | C$_3$ |
| δ = 115.45 ppm | C$_2$ |

EXAMPLE 11

Potassium and methyl phosphonate of bis-(hydroxy-4-phenyl)-1.1-ethyl 32.2 g (0.1 mole) of dimethyl phosphonate of bis-(hydroxy-4-phenyl)-1.1-ethyl are dissolved in 118 ml of a 2.6 N potassium solution.

After having passing a nitrogen feed in the mixture, said mixture is maintained at reflux during 24 hours.

It is proceeded then as in the Example 2.

The obtained products is a hygroscopic powder (which decomposes at about 220°–225° C.).

Elementary analysis (%): C$_{15}$H$_{16}$PO$_5$K

| | P | K |
|---|---|---|
| ~ Calculated | 8.95 | 11.27 |
| ~ Found | 8.44 | 10.70 |

NMR spectrum of the proton (in D$_2$O):

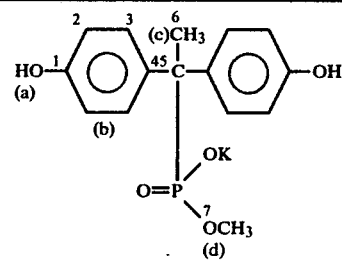

| | |
|---|---|
| δ = 7.5–6.75 ppm (m) | 8HB |
| δ = 3.47 ppm (d) | 3Hd, JP − Hd = 10Hz |
| δ = 1.95 ppm (d) | 3Hc, JP − Hc = 15Hz |

NMR spectrum of the proton (in deuterated DMSO):
The phenolic protons come out at 9.85 ppm.

| | |
|---|---|
| δ = 7.4–6.4 ppm (m) | 8Hb |
| δ = 3.04 ppm (d) | 8Hd, JP − Hd = 9.75 Hz |
| δ = 1.72 ppm (d) | 3Hc, JP − Hc = 13.5 Hz |

NMR of $^{13}$C (in D$_2$O):

| | |
|---|---|
| δ = 156.06 ppm | C$_1$ |
| δ = 140.3–140 ppm | C$_4$ |
| δ = 132.99–132.60 ppm | C$_3$ |
| δ = 117.21 ppm | C$_2$ |
| δ = 55.94–55.22 ppm | C$_7$ |
| δ = 51.36 ppm | C$_5$, JP-C$_5$ = 133.8 Hz |
| δ = 28.45–28.20 ppm | C$_6$ |

EXAMPLE 12

Preparation of diethyl phosphonate of bis-(hydroxy-4-phenyl)-4.4-pentyl

The process proceeds as in Example 1. The obtained product by recrystallisation in the mixture ethyl acetate/-cyclohexane has the following characteristics:
Melting point: 115° C.
Elementary analysis (%): C$_{21}$H$_{29}$PO$_5$

| | C | H | P |
|---|---|---|---|
| ~ Calculated | 64.28 | 7.39 | 7.90 |
| ~ Found | 64.36 | 7.52 | 7.84 |

Infrared spectrum
$\nu P=O = 1\,255$ cm$^{-1}$

NMR spectrum of the proton (deuterated in DMSO as solvent):

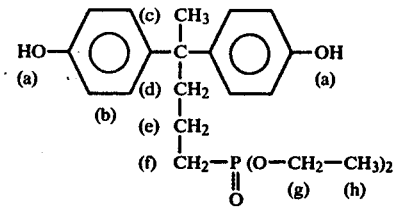

| | |
|---|---|
| δ = 10 ppm (s) | 2Ha |
| δ = 7–6.5 ppm (m) | 8Hb |
| δ = 3.85 ppm (m) | 4Hg |
| δ = 1.45 ppm (s) | 3Hc |
| δ = 1.15 ppm (t) | 6Hh |

The Hd+He+Hf protons give a complex mass of between 2.3 and 1.6 and under Hc and Hh protons.

It should be understood that the invention is not limited to the examples given herein above, and that numerous modifications and variants may be envisaged within the scope of the invention.

What is claimed is:

1. Alkaline hemiesters of bis-(hydroxy-4-phenyl)-alkylphosphonic acids of the general formula:

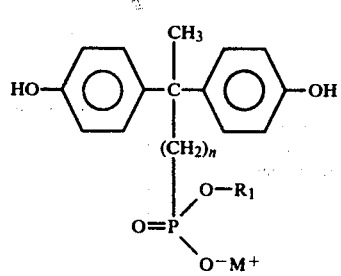

in which:
n is equal to 0, 1, 2 or 3,

M is an alkaline metal such as lithium, sodium or potassium, $R_1$ is cyclohexyl radical or a $C_1$ to $C_6$ alkyl radical.

2. A hemiester according to claim 1, consisting of: sodium and methyl phosphonate of bis-(hydroxy-4-phenyl)-2,2-propyl.

3. A hemiester according to claim 1 consisting of: potassium and methyl phosphonate of bis-(hydroxy-4-phenyl)-2,2-propyl.

4. A hemiester according to claim 1, consisting of: sodium and ethyl phosphonate of bis-(hydroxy-4-phenyl)-2,2-propyl.

5. A hemiester according to claim 1, consisting of: potassium and ethyl bis-(hydroxy-4-phenyl)-2,2-propyl.

6. A hemiester according to claim 1, consisting of: sodium and methyl phosphonate of bis-(hydroxy-4-phenyl)-3,3-butyl.

7. A hemiester according to claim 1, consisting of: sodium and methyl phosphonate of bis-(hydroxyphenyl)-1,1-ethyl.

8. A hemiester according to claim 1, consisting of: potassium and methyl phosphonate of bis-(hydroxy-4-phenyl)-1,1-ethyl.

* * * * *

UNITED STATES PATENT AND TRADEMARK OFFICE
CERTIFICATE OF CORRECTION

PATENT NO. : 4,272,457
DATED : June 9, 1981
INVENTOR(S) : Pierre Poisson and Georges Sturtz It is certified that error appears in the above—identified patent and that said Letters Patent is hereby corrected as shown below:

Column 1, line 24, please delete "R" and insert --$R_1$--.

Column 1, line 47, after "$R_1$ and $R_2$ are" please insert --cyclohexyl radical or--.

Column 6, line 61, please delete "ethyl 1/2 acetate" and insert --ethyl acetate--.

Column 7, line 27, please delete "$\nu$p-O-C" and insert --$\nu$P-O-C--.

Column 8, line 37, please delete "sodium" and insert --potassium--.

Column 9, line 67, after "133.8" please insert --$H_z$--.

Column 10, line 11, please delete "KOH" and insert --NaOH--.

Column 11, line 32, after "potassium" please insert --hydroxide--.

Column 11, line 33, please delete "passing" and insert --passed--.

Signed and Sealed this

Twentieth Day of October 1981

[SEAL]

Attest:

GERALD J. MOSSINGHOFF

*Attesting Officer*  *Commissioner of Patents and Trademarks*